United States Patent [19]

Ojima et al.

[11] 4,319,542

[45] Mar. 16, 1982

[54] APPARATUS FOR PREPARATION OF BLOOD SMEAR SPECIMENS

[75] Inventors: Katsuhiro Ojima; Hajime Matsushita; Isao Fujimoto; Satosi Mizuno; Tsuyoshi Nishida, all of Katsuta, Japan

[73] Assignees: Agency of Industrial Science & Technology; Ministry of International Trade & Industry, both of Tokyo, Japan

[21] Appl. No.: 127,470

[22] Filed: Mar. 5, 1980

[51] Int. Cl.³ ............................................. B05C 11/04
[52] U.S. Cl. .................................. 118/100; 118/236; 118/238
[58] Field of Search ............... 118/100, 238, 108, 120, 118/236; 427/2, 4; 424/3; 221/135

[56] References Cited

U.S. PATENT DOCUMENTS 3,589,557  6/1971  Johnson ......................... 118/100 X
3,888,206  6/1975  Faulkner ........................... 118/100

Primary Examiner—John P. McIntosh
Attorney, Agent, or Firm—Oblon, Fisher, Spivak, McClelland & Maier

[57] ABSTRACT

An apparatus for the preparation of blood smear specimens is constructed to successively discharge glass slides from a stack. A first glass slide is laid horizontally near the point of discharge and a second glass slide is discharged into a slanted position with its lower edge in contact with the leading end of horizontal glass slide. A drop of blood is applied near the leading end of the horizontal glass slide behind the position of contact of the glass slide in the slanted position and the horizontal glass slide is advanced to smear the blood onto the horizontal slide using the slanted glass slide as a coater. The slanted glass slide is then allowed to fall into the horizontal position and another glass slide is discharged from the stack into the slanted position, whereafter the process is repeated.

3 Claims, 6 Drawing Figures

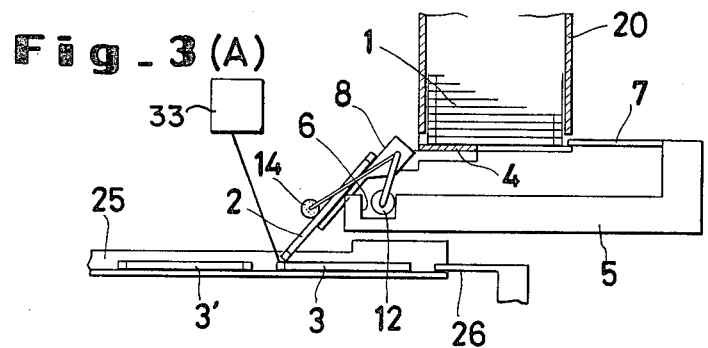
Fig_3 (A)
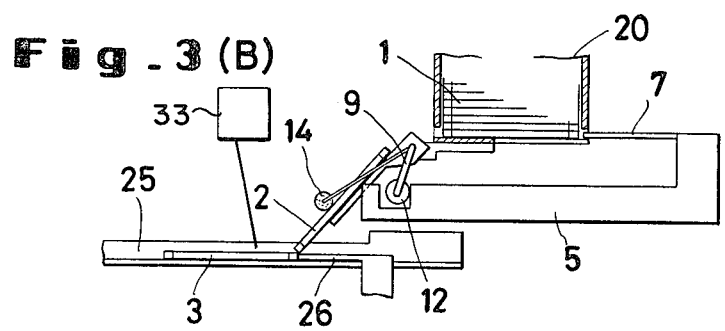
Fig_3 (B)
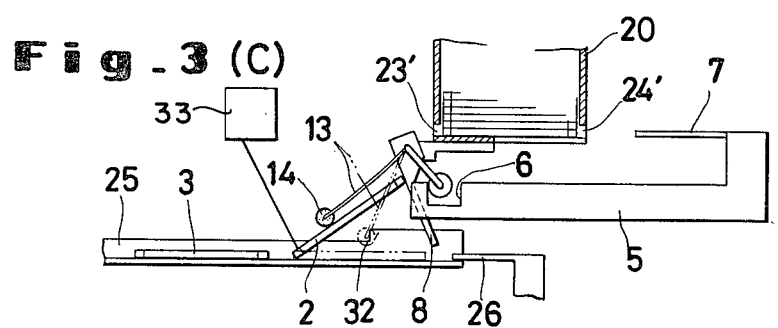
Fig_3 (C)
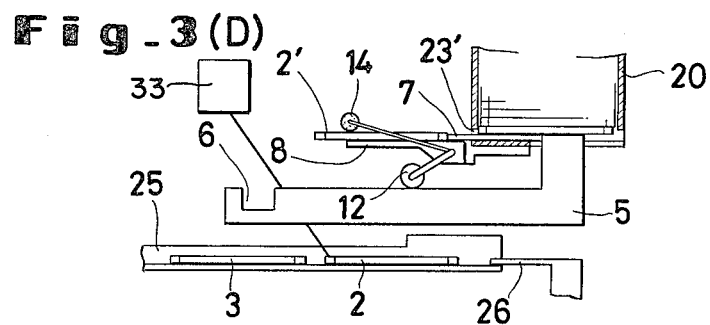
Fig_3 (D)

APPARATUS FOR PREPARATION OF BLOOD SMEAR SPECIMENS

BACKGROUND OF THE INVENTION

This invention relates to an apparatus for the preparation of blood smear specimens, suitable for the formation of stained films of blood on the surface of glass slides for the microscopic observation of blood corpuscles.

In diagnosing a disease, it is a common practice to submit a blood sample from the patient to a test to determine such factors as the form and distribution of white blood corpuscles and red blood corpuscles in the blood sample. This test is effected by a procedure comprising the steps of spreading the blood sample in a thin film on the surface of a glass slide to produce a blood smear specimen, staining the blood smear specimen as required, and observing the stained blood smear through a microscope to determine the form and distribution of the blood corpuscles.

As typical mechanical methods available for the application of blood smears to the surface of glass slides, there have been known the spinner method (U.S. Pat. No. 3,705,048, for example,) and the wedge method. In the spinner method the application of the blood smear is effected by placing the blood sample on a glass slide and spinning the glass slide around the center of the slide thereby causing the sample blood to be centrifugally dispersed into a film on the slide surface. To produce a blood smear in a film of uniform thickness on the surface of a glass slide, by the spinner method the amount of blood sample placed on the glass slide must be so large that some excess blood flies away from the slide surface during spinning. This method, thus requires a large blood sample (generally more than 100 times the amount of blood actually applied to the blood smear) and calls for the extra step of safely disposing of the excess blood spun of the slide. It further entails the problem of possible deformation, destruction, etc. of the blood corpuscles due to the centrifugal force applied thereto during the spinning of the slide.

The wedge method disclosed in Japanese Utility Model Disclosure No. 31545/1977 has resulted from the mechanization of a method heretofore performed by a manual procedure comprising the steps of placing a given blood sample on the surface of a glass slide and then causing a cover glass provided on the glass slide to be moved relative to the glass slide so that one of the longitudinal edges thereof will spread the blood into a thin film on the surface of the glass slide. According to this method, however, since part of the blood used in each application of blood smear remains on the cover glass at the end of the application, the remaining blood must be removed from the cover glass before the cover glass is put to use in the next blood smear application. This method, therefore, has necessitated the extra work of removing the remaining blood from the cover glass by wiping the cover glass with a wad of cotton impregnated with methanol or some other suitable alcohol each time the application of a blood smear is carried out. Thorough removal of the remaining blood by this wiping work has proved to be difficult. Moreover, there is a possibility that proteins and fats originating in various blood samples will accumulate and adhere to the longitudinal edge of the cover glass even to a point where the cover glass will fail to retain the longitudinal edge in a condition appropriate for the preparation of blood smear specimens.

In view of the problems inherent in known methods for preparation of blood smear specimens, it is one object of this invention to provide an apparatus for the preparation of blood smear specimens free from the effects of blood remaining from previous blood application and from the effects of adhesion of proteins and fats.

Another object of this invention is to provide an apparatus for speedy preparation of blood smear specimens wherein blood samples are smeared substantially uniformly.

SUMMARY OF THE INVENTION

To accomplish the objects described above according to this invention, there is provided an apparatus for the preparation of blood smear specimens, which comprises a storage box for a plurality of fresh glass slides, means for discharging the glass slides one by one from the storage box, means for receiving each glass slide discharged from the storage box and holding it in a slanted position, means for transferring the obliquely held glass slide into a horizontal position, means for placing drop of blood sample onto the horizontally held glass slide and means for removing the glass slide smeared with the blood sample. As a given glass slide is set in the slanted position, its lower edge is brought into contact with the leading edge portion of the immediately preceding glass slide which has already been transferred the horizontal position. After this contact is established, a sample of blood is dropped near the leading-edge portion of the horizontally held glass slide. Then, the horizontally held glass slide is moved forward with the lower edge of the glass slide in the slanted position kept in contact with the surface thereof with the result that the blood is spread out on the horizontal glass slide. The result is a blood smear specimen suitable for microscopic observation. Now, the horizontal glass slide having the blood smear formed thereon is removed and the glass slide in the slanted position is transferred to the horizontal position by being rotated about its lower edge. Thereafter, another glass slide freshly discharged out of the storage box is brought into the slanted position with the lower edge thereof brought into contact with the leading-edge portion of the horizontally held glass slide. The next blood sample is applied in the same manner to produce a new blood smear specimen.

As described above, the apparatus of the present invention operates on the principle that each glass slide freshly discharged from the storage box has its leading edge utilized as the coater for spreading the blood on the surface of the immediately preceding glass slide and the glass slide, after being used as the coater, is wholly utilized as the slide for the formation of a blood smear. Because of this operating principle, the blood smear specimens produced by the present apparatus are free from otherwise possible contamination by residual blood and the individual glass slides have no need for a device for wiping off residual blood prior to application of a fresh blood sample. The present invention, therefore, allows blood smear specimens to be produced with high efficiency. The apparatus of this invention has another advantage in that since the angle of the slanted glass slide serving as the coater and the speed at which the slanted glass slide is moved relative to the surface of the horizontal glass slide are the same in all successive operations, the conditions of the blood smears formed on all the specimens obtained by this apparatus are identical insofar as the amounts of blood sample dropped onto the successive horizontal glass slides are equal.

The other objects and characteristics of the present invention will become apparent from the further disclosure of the invention to be made hereinafter with reference to the accompanying drawing.

BRIEF EXPLANATION OF THE DRAWING:

FIGS. 3(A), (B), (C) and (D) are explanatory diagrams illustrating serially the preparation of a blood smear specimen by the operation of the apparatus shown in FIG. 1.

Figure 1:
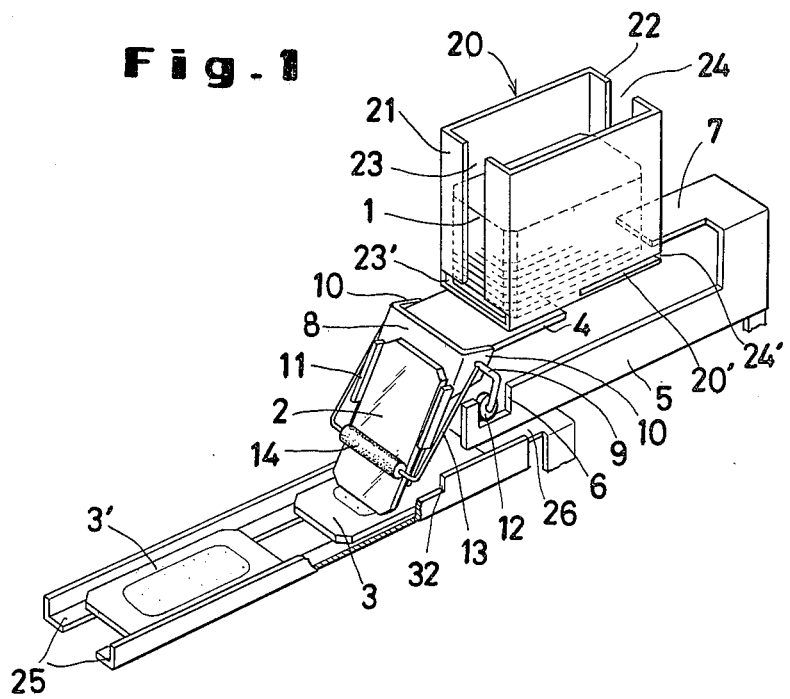
FIG. 1 is a perspective view illustrating the construction of one embodiment of the apparatus for the preparation of blood smear specimens according to the present invention.

DESCRIPTION OF THE PREFERRED EMBODIMENT:

Referring to the drawing, a plurality of glass slides 1 are stored in a storage box 20 which is open at the top. In the front wall 21 and the rear wall 22 of the box 20, openings 23, 24 are formed in the vertical direction for the purpose of facilitating the insertion of the plurality of glass slides into the box and permitting constant inspection of the supply of glass slides 1 held inside the box. At the lowermost ends of the front wall 21 and the rear wall 22 of the storage box 20, slits 23', 24' each capable of permitting passage of one glass slide are formed respectively in the horizontal direction. The storage box 20 for the glass slides is made of a suitable material such as, for example, wood, synthetic resin or metal. Inside the box, a multiplicity of clean, unused glass slides are piled up one on top of another. This storage box 20 is supported by suitable means to a base 4.

Figure 2:
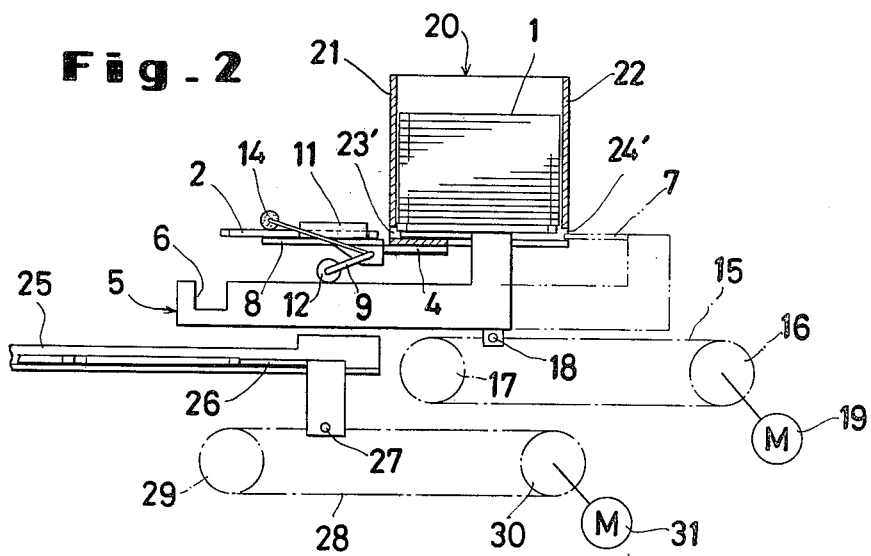
FIG. 2 is a partially sectioned side view of the apparatus for the preparation of blood smear specimen shown in FIG. 1.

Below the storage box 20 is disposed a plate cam 5 which is provided toward the front edge of the upper face thereof with notch 6 and toward the rear edge of the upper face thereof with a plunger plate 7. The aforementioned plunger plate 7 is disposed horizontally and connected through the medium of a rising portion to the rear end of the plate cam 5. The plunger plate 7 has a width equal to or slightly smaller than the width of the glass slides and a thickness slightly smaller than the thickness of the glass slides. The plunger plate 7 is disposed so that the leading end thereof is directly opposed to the horizontal slit 24' formed at the lowermost end of the rear wall 22 of the storage box 20. Below this plate cam 5 is disposed an endless belt 15 stretched taut by pulleys 16, 17 (FIG. 2). A pin 18 fixed on the belt 15 is engaged with the plate cam 5, so that the plate cam 5 is caused to produce a reciprocating motion within guide rails (not illustrated) by the forward and backward rotation of a motor 19 to which the pulley 16 is interlocked. Consequently, the plunger plate 7 is thrust into the storage box 20 to push the lowermost of the stack of glass slides through the slit 23' in the front wall 21 of the storage box. In the case of the illustrated embodiment, the plunger plate 7 is adapted so as to be inserted through the slit 20' formed in the lower portion of the lateral wall of the storage box to the interior of the storage box.

To the leading end of the base 4 on which the storage box 20 for the glass slides 1 is fastened, a holder plate 8 is pivotally attached rotatably relative to the base 4 by means of a shaft 9 protruding in opposite directions from a bearing plate 10 formed by folding back the holder plate 8. On the opposite lateral edges of the aforementioned holder plate 8, folded portions 11 are provided one each for the purpose of preventing the glass slides from sustaining abrasion on their lateral edges. One of the opposite protruding ends of the aforementioned shaft 9 is bent and is provided at its tip with a roller 12 which is adapted to rotate through contact with the plate cam 5. The bearing plates 10 are further provided with a spring shaft 13, and the free ends of the spring shaft 13 are provided at the leading side thereof with a rubber roller 14 supported in a freely rotatable condition. The spring shaft 13 is adapted to have the rubber roller 14 constantly pressed against the holder plate 8 with some degree of resilient force. When the plate cam 5 produces its reciprocating motion, therefore, the roller 12 rotates on the plate cam while holding the holder plate 8 in its horizontal position (FIG. 2). When the roller 12 is caught in the notch 6, the holder plate 8 is pivoted with the shaft 9 as the fulcrum. In the meantime, the glass slide is pressed against the holder plate 8 by the rubber roller 14 and remains stationary relative to the holder plate.

Below the holder plate 8 are provided guide rails 25. The guide rails are separated from each other by a distance substantially equal to the width of the glass slides. A push plate 26 which is provided at the rear end of the guide rails 25 is engaged through the medium of a pin 27 with an endless belt 28 stretched taut between pulleys 29, 30. In consequence of the forward and backward rotation of a motor 31 interlocked with the pulley 30, the push plate 26 produces a reciprocating motion within the guide rails 25. Optionally, the guide rails may be provided with stepped portions 32 which serve the purpose of obstructing the rotary motion of the spring shaft 13.

The step for the application of blood smear to the glass slides will now be described below in relation to the overall operation of the apparatus for the preparation of blood smear specimens according to the present invention.

As illustrated in FIG. 1, the glass slide 3 to be smeared with the blood sample is laid level between the guide rails 25 and the glass slide 2 to be utilized as the coater is held in a slanted position by the holder plate 8 in such a manner that the lower leading end thereof remains in intimate contact with the leading-edge portion of the glass slide 3 as shown in FIG. 3(A). (In FIG. 3, the folded portions 11 have been omitted to more clearly illustrate the slide glass.) The angle formed between the two glass slides 2, 3 is desired to fall in the neighborhood of 60°.

After the two glass slides have assumed the positions described above, the given blood sample is dropped by dropper 33 near the leading edge of the glass slide 3 at a position behind that at which the lower leading edge of the glass slide 2 makes oblique contact. Then the rotation of the motor 31 causes the push plate 26 to move forward within the guide rails 25 and, consequently, causes the glass slide 3 to move forward. The result is that the edge portion of the glass slide 2 spreads the drop of blood over the glass slide 3. After the sliding of the edge portion of the glass slide 2 has covered the entire surface of the glass slide 3 (FIG. 3(B)), there exists a thin film of blood smear specimen on the surface of the glass slide 3. Then, the push plate 26 is returned to the righthand end of the guide rails 25 by the backward rotation of the motor 31 and is held in this position until a blood smear is to be applied to the next glass slide.

The aforementioned application of the drop of blood sample to the horizontal glass slide 3 may also made either prior to or simultaneously with the establishment of mutual contact between the two glass slides 2 and 3.

Subsequently, the motor 19 is rotated backwardly to have the plate cam 5 moved backwardly (in the righthand direction with reference to the drawing). In consequence of the backward travel of the plate cam 5 mentioned above, the roller 12 caught in the notch 6 is moved and the holder plate 8 and the spring shaft 13 are caused to rotate counterclockwise (as seen in the figures) around the shaft 9. At this time, since the edge portion of the glass slide 2 is retained in contact with the guide rails 25, the rotation of the holder plate causes the rear face of the glass slide 2 to separate gradually from the holder plate 8 (FIG. 3(C)).

As the rotation of the holder plate 8 continues further, the rear face of the glass slide 2 to eventually deprived of the support provided by the holder plate 8 and is consequently laid level on the guide rails 25 to await the application of the next blood sample. The spring shaft 13 causes to apply pressure to the glass slide when it collides with the stepped portion 32 of the guide rails 25. At the same time, the leading end of the plunger plate 7 retracts from the storage box 20 for glass slides 1 through the slit 23'.

At the time that the next glass slide 2 for application of a blood smear is laid levelly on the guide rails 25, the motor 19 is rotated in the forward direction to have the plate cam 5 moved forward. By this forward motion of the plate cam, the holder plate 8 and the spring shaft 13 are rotated clockwise to temporarily assume the condition shown in FIG. 3(B). The further advance of the plate cam 5 causes the roller 12 to escape from the notch 6 and start rolling on the upper edge surface of the plate cam 5 and consequently causes the holder plate 8 to be laid in a horizontal position with the rubber roll 14 maintained in direct contact therewith. In the meantime, the leading end of the plunger plate 7 enters the slit 24' formed the rear wall 22 of the storage box 20 and causes the lowermost of the stack of glass slides 1 held within the storage box to be pushed out of the storage box through the slit 23' formed in the front wall 21. The glass slide thus pushed out by the plunger plate 7 is inserted between the holder plate 8 and the rubber roll 14. After the glass slide 2' has been retained perfectly in position on the holder plate 8 (FIG. 3(D)), the motor 19 is again rotated backwardly to have the plate cam moved backwardly to a position at which the roller 12 is are caught in the notch 6. After the roller 12 has been completely received in the notch 6, the holder plate 8 is slanted and the glass slide held therein falls slowly under its own weight within the holder plate. The fall of the glass slide stops at the moment that the leading edge thereof comes into contact with the glass slide already said levelly within the guide rails.

With the motion of the glass slide mentioned above, the apparatus assumes the condition of FIG. 1 (FIG. 3(A)) again. At this time, the next blood sample is dropped onto the glass slide held levelly between the guide rails and the procedure described above is repeated to produce another blood smear specimen.

As is clear from the foregoing description, in the apparatus for the preparation of blood smear specimens according to the present invention, each glass slide discharged from the storage box is first brought into a slanted position and utilized as the coater for a blood sample applied to the immediately preceding glass slide laid beforehand in a horizontal position and, after the application of the blood sample, that glass slide is laid into the horizontal position and used as the substrate for the application of the next blood sample as a thin blood smear by using the newly discharged glass slide as the coater. This apparatus, therefore, has no need for the stationary coater required by the conventional apparatus and permits each blood sample to be spread with a new coater in every application of the blood smears. The blood smear specimens produced by this apparatus, accordingly, are free from possible contamination by residual blood or accumulation of proteins and fats. The apparatus as a whole enjoys simplicity of construction and assures sanitary operation because it requires no device for cleaning a incorporated separately coater. Addition of means capable of forwarding signals in a suitable sequence to the two motors and to the device for placing drops of blood on the glass slides successively laid in a horizontal position permits the apparatus of this invention to provide automatic preparation of blood smear specimens.

What is claimed is:

1. An apparatus for the preparation of blood smear specimens consisting of thin films of blood formed on glass slides for microscopic observation, which apparatus comprises:

a storage box for a stack of clean glass slides, means for discharging the glass slides one by one from said storage box, means for receiving a glass slide discharged from said storage box and setting said slide in an oblique position, means for transferring the obliquely held glass slide to the horizontal position by rotating said slide about the lower leading edge thereof, whereby the lower edge of a subsequently discharged and obliquely held glass slide may be brought into contact with the leading edge portion of the previously discharged and horizontally held glass slide, means for placing drop of blood sample on the glass slide in the horizontal position, and means for causing the horizontally held glass slide having the drop of blood sample retained thereon to be moved forward while keeping the upper surface thereof in contact with the lower edge of the obliquely held glass slide.

2. The apparatus according to claim 1, wherein the means for placing the drop of blood sample is so adapted that the drop lands near the leading edge portion of the glass slide.

3. The apparatus according to claim 1, wherein said means for discharging, means for receiving, means for transferring and means for causing are adapted so that the obliquely held glass slide is transferred to the horizontal position and a freshly discharged glass slide is received and set into an oblique position with the lower edge thereof brought into contact with the horizontally held glass slide after the glass slide having the drop of blood sample held on the upper surface thereof has been moved forward.

* * * * *

UNITED STATES PATENT AND TRADEMARK OFFICE
CERTIFICATE OF CORRECTION

PATENT NO. : 4,319,542
DATED : Mar. 16, 1982
INVENTOR(S) : Katsuhiro Ojima, et. al.

It is certified that error appears in the above—identified patent and that said Letters Patent is hereby corrected as shown below:

On The Title Page insert:

-- [30]---Foreign Application Priority Data

Jul. 9, 1979 [JP]  Japan .............. 54-85986   --.

Signed and Sealed this

Twenty-fifth Day of May 1982

[SEAL]

Attest:

Attesting Officer

GERALD J. MOSSINGHOFF

Commissioner of Patents and Trademarks